United States Patent [19]

Ferrari et al.

[11] 4,287,211

[45] Sep. 1, 1981

[54] DERIVATIVES OF PHENYLETHYLAMINES, PROCESSES FOR THEIR PREPARATION AND RELATED PHARMACEUTICAL COMPOSITIONS

[75] Inventors: Giorgio Ferrari; Vittorio Vecchietti, both of Milan, Italy

[73] Assignee: Simes, S.p.A., Milan, Italy

[21] Appl. No.: 108,157

[22] Filed: Dec. 28, 1979

[30] Foreign Application Priority Data

Jan. 23, 1979 [IT] Italy ............................. 19531 A/79

[51] Int. Cl.$^3$ ..................... A61K 31/17; C07C 127/19
[52] U.S. Cl. ...................................... 424/322; 564/51
[58] Field of Search ................... 260/553 A; 424/322; 564/51

[56] References Cited

U.S. PATENT DOCUMENTS 4,058,557  11/1977  Douglas et al. ...................... 424/322

Primary Examiner—Frederick E. Waddell
Attorney, Agent, or Firm—Cushman, Darby & Cushman

[57] ABSTRACT

Novel derivatives of phenylethylamine, having general formula:

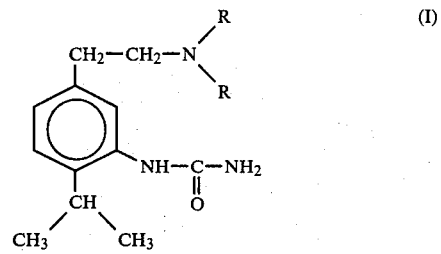

wherein R is hydrogen or a lower alkyl, are disclosed, to be used in the therapy of diseases of the digestive apparatus, particularly gastric and/or duodenal ulcers. The novel derivatives of phenylethylamine are prepared
(a) from a compound of formula (II)

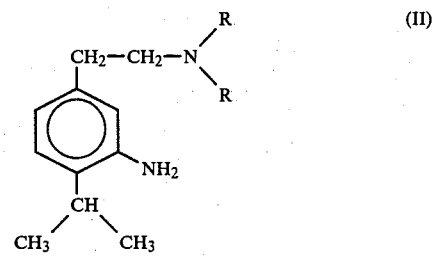

by reaction with potassium cyanate, in the presence of an organic acid;
(b) from the compound of formula (II) which is converted to the corresponding phenylcarbonic derivative by reacting with phenylchloroformiate and then with ammonia
(c) from a compound of formula (IV)

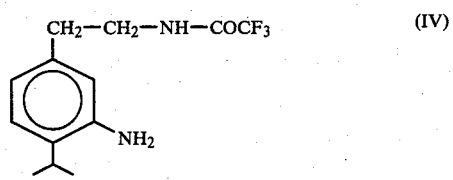

which is converted to a compound of formula (V), the latter being converted to the desired derivatives (I) by treatment with aqueous alkali.

15 Claims, No Drawings

DERIVATIVES OF PHENYLETHYLAMINES, PROCESSES FOR THEIR PREPARATION AND RELATED PHARMACEUTICAL COMPOSITIONS

The present invention relates to a new class of compounds having biological activity, owing to which they are useful as novel therapeutical agents. The novel compounds are derivatives of phenylethylamines, substituted in the aromatic ring and in the amine group of the side chain, having general formula (I):

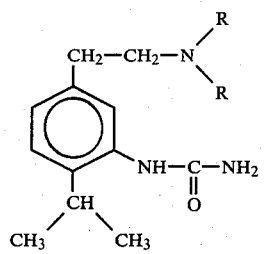

wherein R is hydrogen, methyl, ethyl, propyl. The novel substances are endowed with a remarkable biological activity, and particularly with a noticeable anti-ulcer activity.

The novel compounds of formula (I) can be prepared by reaction of potassium cyanate with a compound of formula (II)

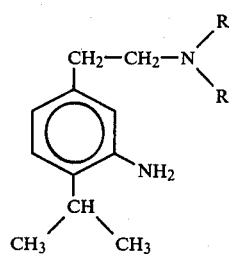

wherein R has the above mentioned meaning. The reaction takes place in a particularly good manner in suitable solvents, such as methanol, tetrahydrofuran and dioxane, in admixture in proper proportions with water and in the presence of suitable organic acids, such as formic acid, acetic acid, propionic acid at temperatures of between −10° C. and +50° C. It has been furthermore found that the compounds of formula (I) can be prepared, still starting from the compounds of general formula (II), but through an indirect way.

There is firstly prepared the phenylcarbonic compound, of general formula (III)

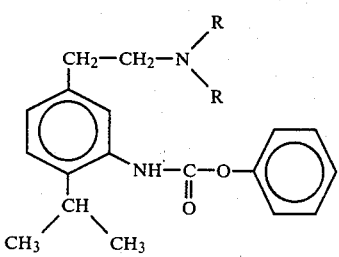

by reacting a compound of formula (II) with phenylchloroformiate in suitable solvents, such as methylene chloride chloroform, tetrahydrofuran, in the presence of organic bases, such as triethylamine or pyridine at a temperature of between −25° C. and +25° C. By treating with ammonia the resulting compound, in a suitable solvent such as dimethylformamide or dimethyl sulphoxide at a temperature of between −10° C. and +25° C., the compounds of formula (I) are obtained.

Lastly, in the case in which in the compounds of general formula (I) R is hydrogen, it has been found that the above described reactions can take place with a compound of general formula (IV):

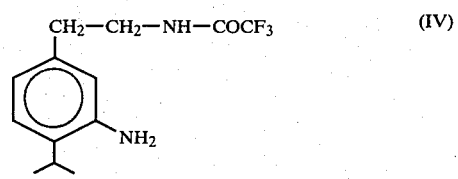

thus obtaining compounds of formula (V)

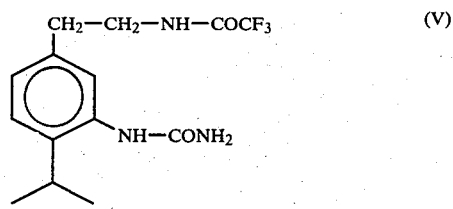

It has been found that the compounds (V) upon treatment with diluted alkali (KOH or NaOH in aqueous methanol, ethanol or dioxane) give the compounds of formula (I) in which R=H.

The intermediate compounds, having the formula (VI) and (VII) as hereinafter indicated and necessary for the above described reactions, are in turn novel substances and can be prepared, by means of generally known methods, according to the following scheme, for the several desired compounds:

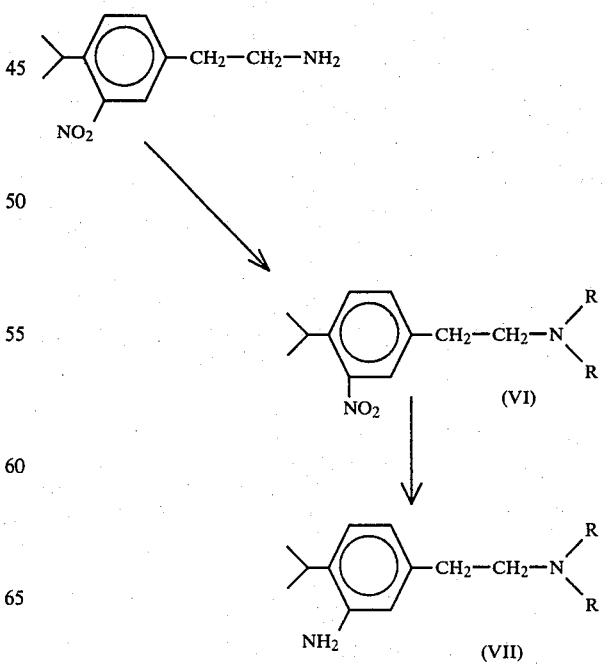

In the following examples, having only illustrative but non limiting meaning, the detailed information, needed for obtaining the novel compounds of the present invention, are given, these compounds being crystalline substances and forming with pharmaceutically acceptable organic and inorganic acids salts which in turn are crystalline too.

EXAMPLE 1

7 grams of 4-isopropyl-3-nitro-benzylcyamide (Kp 120–130/0.1 mm, IR (NaCl) 2260 cm$^{-1}$) are reduced with NaBH$_4$ and BF$_3$.Et$_2$O according to the method described in J. Med. Chem., 11, 21, 1968, giving place to 4.7 g of 4-isopropyl-3-nitro-phenylethylamine hydrochloride (compound n. 1), m.p.=214°–216° C. (EtOH/ether), M+208.

EXAMPLE 2

A solution of 18 g of 4-isopropyl-3-nitro-phenylethylamine hydrochloride in 150 mls of dimethylformamide it treated with 15,6 g of Na$_2$CO$_3$ and 14.8 mls of n-propyl bromide. The reaction mixture is heated for 4 hours at 50°–60° C. and then supplemented with 3 g of Na$_2$CO$_3$ and 3 mls of n-propyl-bromide, by continuing the heating for further 5 hours. The reaction mixture is then poured in water, and extracted several times with ether. The organic extracts is firstly dried over Na$_2$SO$_4$ and then treated with a stream of hydrogen chloride gas. The resulting solid product is filtered and crystallized from acetone/ethyl ether, thus obtaining 12.1 g of N,N-dipropyl-(4-isopropyl-3-nitro)-phenylethylamine (compound n. 2), m.p. 115°–117° C.

Likewise there are prepared:
N,N-dimethyl-(4-isopropyl-3-nitro)-phenylethylamine HCl, m.p. 157°–160° C. (compound n. 3)
N,N-diethyl-(4-isopropyl-3-nitro)-phenylethylamine HCl, m.p. 198°–202° C., (compound n. 4)

EXAMPLE 3

A solution of 1.6 g of 4-isopropyl-3-nitro-phenylethylamine in 20 mls of benzene is supplemented with 1.07 mls of trifluoroacetic anhydride, the mixture being then heated to 60° C. for 4 hours. The reaction mixture is thereafter cooled, woshed with a 5% NaHCO$_3$ solution and concentrated to dryness.

The solid residue is crystallized from petroleum ether 80°–100° C., thus obtaining 2 g of N-trifluoroacetyl-(4-isopropyl-3-nitro)-phenylethylamine (compound n. 5), m.p. 56°–57° C., M+304.

EXAMPLE 4

9.8 g of N,N-dimethyl-(4-isopropyl-3-nitro)-phenylethylamine in alcohol solution are hydrogenated in a Parr type hydrogenation equipment, in the presence of 0.5 g of palladium on 10% carbon and under 50 psi pressure (about 3.5 kg/sq.cm).

Upon the absorption is completed, the catalyst is filtered, and an excess of 10% HCl is added to the filtrate, the reaction mixture being then evaporated to dryness, thus obtaining N,N-dimethyl-(3-amino-4-isopropyl)-phenylethylamine dihydrochloride (compound n. 6).

Likewise there are prepared:
N-trifluoroacetyl-(3-amino-4-isopropyl)-phenylethylamine hydrochloride (compound n. 7).
N,N-diethyl-(3-amino-4-isopropyl)-phenylethylamine dihydrochloride compound n. 8).
N,N-dipropil-(3-amino-4-isopropyl)-phenylethylamine dihydrochloride (compond n. 9).

EXAMPLE 5

A solution of 5.5 g of N,N-dipropyl-(3-amino-4-isopropyl)-phenylethylamine in 25 mls of methylene chloride is serially treated with 2.54 mls of pyridine and 2.92 mls of phenyl chloroformiate. After 2 hour stirring at room temperature, the reaction mixture is diluted with further methylene chloride, and then washed with water and a bicarbonate solution. After evaporation of the solvent there are obtained 9 g of a dense oil, essentially consisting of the corresponding phenyl urethane. This raw product, without further purification, is dissolved in 50 mls of dimethyl formamide and treated with slow stream of carbon dioxide gas; after 30 minutes the reaction is completed. The reaction mixture is poured in water and extracted firstly with ethyl ether, the extract being discarded, and then with ethyl acetate.

By evaporating the latter, there are obtained 6.2 g of solid product which is crystallized from ethyl acetate/ligroin, thus obtaining N,N-dipropyl-(4-isopropyl-3-ureido)-phenylethylamine, (compound n. 10), m.p. 128°–129° C.

Likewise there are prepared:
N-trifluoroacetyl-(4-isopropyl-3-ureido)-phenylethylamine, (compound n. 11), m.p. 63°–65° C. N,N-dimethyl-(4-isopropyl-3-ureido)-phenylethylamine, (compound n. 12), m.p. 146°–148° L C.
N,N-diethyl-(4-isopropyl-3-ureido))phenylethylamine, (compound n. 13), m.p. 146°–147° C.

EXAMPLE 6

A solution of 4.7 g of N-trifluoroacetyl-(4-isopropyl-3-ureido)-phenylethylamine in 80 mls of methanol, containing 3.2 g of NaOH dissolved in 15 mls of water, is heated to reflux for 30 minutes.

The reaction mixture is evaporated to dryness under reduced pressure and the residue is filtered on a short SiO$_2$ column, CH$_2$Cl$_2$/MeOH (9:1) being used as the eluant. After evaporation of the combined eluates, there are obtained 2.8 g of oily product, which after treatment with maleic acid in methanol gives 4-isopropyl-3-ureido-phenylethylamine maleate, (compound n. 14), m.p. 122°–125° C.

EXAMPLE 7

1 g of N,N-dimethyl-(3-amino-4-isopropyl)-phenylethylamine, dissolved in 15 mls of methanol containing 3 mls of acetic acid, are cooled to 5° C. and treated with 1 g of KNCO dissolved in 2 mls of water. The reaction mixture is maintained on standing for 15 hours at 5°–10° C. and then evaporated to a small volume under reduced pressure; then it is made basic with solid Na$_2$CO$_3$ and extracted with ethyl acetate. The combined organic extracts are chromatographed on SiO$_2$ with methylene chloride containing increasing amounts of methanol. The homogeneous fractions are combined and concentrated, the residue being crystallized from ethyl acetate/ligroin, giving place to 150 mg of compound n. 12, melting at 146°–148° C., identical to that prepared according to the example 5.

Likewise are prepared the other derivatives listed in the same example.

In the tests of biological activity it has been found that generally the compounds having general formula (I) are able to prevent the several experimental gastric ulcers from being formed.

Such an activity is even more interesting owing to the fact that it is not accompanied by physiological effects of different nature, whereby a specific anti-ulcer activity does result. The novel compounds, moreover, are scarcely toxic.

More particularly the compound n. 12, N,N-dimethyl-(4-isopropyl-3-ureido)-phenylethylamine, has a $DL_{50}$ of 500 mg/kg/os in the rat. The some compound, when experimented in the ulcer test according to Buche et Gallaire (Compt. Rend. Soc. Biol., 157, 1225, (1963)) shows, in the rat at the dose of 50 mg/kg/os, an inhibition of the ulcer index higher than 80%.

The same compound, when compared with chloropromazine, (the latter substance being used as the reference in the advanced pharmacological tests for the ulcer) gives place to the following results, still in the rat:

| Compound n. | dose mg/kg/os | inhibition % |
|---|---|---|
| 12 | 5 | 25 |
| 12 | 10 | 53 |
| 12 | 25 | 77 |
| chloropromazine | 20 | 71 |

The particularly favourable therapeutical index, resulting from the pharmacological data, renders this compound particularly suitable for the pharmaceutical use. To this end, the compound n. 12, suitably formulated for the therapeutical use, can be employed as the active drug in the treatment of diseases of the digesting apparatus, such as gastric and/or duodenal ulcers, gastritis, etc. The doses can be comprised between 10 and 250 mg.

For the use as a drug the compounds of the invention of formula (I) can be formulated as preparations for oral and parenteral use, as well as in form of suppositories, the compounds being admixed with or dissolved in suitable vehicles or solvents to obtain capsules, tablets, pills, soft gelatin capsules, injectable vials, solutions for dropwise administration, suspensions, syrups and suppositories.

The preparations can also be formulated for the time delayed release.

We claim:

1. A derivative of phenylethylamine, substituted in the aromatic ring and in the amino group of the side chain, having the general formula:

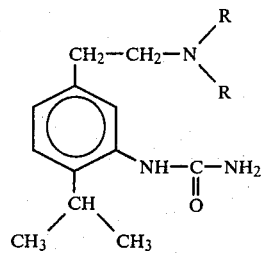

wherein R is hydrogen or a lower alkyl.

2. Derivative of phenylethylamine according to claim 1, which is N,N-dipropyl-(4-isopropyl-3-ureido)-phenylethylamine.

3. Derivative of phenylethylamine according to claim 1, which is N,N-dimethyl-(4-isopropyl-3-ureido)-phenylethylamine.

4. Derivative of phenylethylamine according to claim 1, which is N,N-diethyl-(4-isopropyl-3-ureido)-phenylethylamine.

5. Derivative of phenylethylamine according to claim 1, which is 4-isopropyl-3-ureido-phenylethylamine.

6. A pharmaceutical composition for the therapy of diseases of the digestive apparatus, particularly gastric and/or duodenal ulcers, gastritis, etc., characterized by containing, as the active ingredient an effective amount of a derivative of phenylethylamine according to claim 1 and a suitable pharmaceutical vehicle.

7. A pharmaceutical composition according to claim 6, characterized in that said derivative is N,N-dimethyl-(4-isopropyl-3-ureido)-phenylethylamine.

8. A pharmaceutical composition according to claim 7, characterized in that the dosage of the derivative of phenylethylamine is 10 to 250 mg.

9. A pharmaceutical composition according to claim 8, characterized in that it is in form suitable for oral, parenteral or rectal use, in combination with suitable solvent and/or excipients, of normal use in the pharmaceutical art.

10. A process for the treatment of gastritis, gastric ulcers and duodenal ulcers comprising administering an amount of a compound of claim 1 effective for such purpose.

11. A process according to claim 10, wherein there is administered a dose between 10 and 250 mg.

12. A process for the treatment of gastritis, gastric ulcers and duodenal ulcers comprising administering an amount of the compound of claim 2 effective for such purpose.

13. A process for the treatment of gastritis, gastric ulcers and duodenal ulcers comprising administering an amount of the compound of claim 3 effective for such purpose.

14. A process for the treatment of gastritis, gastric ulcers and duodenal ulcers comprising administering an amount of the compound of claim 4 effective for such purpose.

15. A process for the treatment of gastritis, gastric ulcers and duodenal ulcers comprising administering an amount of the compound of claim 5 effective for such purpose.

* * * * *